US008194944B2

(12) United States Patent
Tivig et al.

(10) Patent No.: US 8,194,944 B2
(45) Date of Patent: Jun. 5, 2012

(54) METHOD OF AUTOMATICALLY DISPLAYING MEDICAL MEASUREMENT DATA (75) Inventors: Gerhard Tivig, Böblingen (DE); Alejo Costa Ribalta, Stuttgart (DE); Andreas Bindszus, Böblingen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 10/595,431

(22) PCT Filed: Oct. 12, 2004

(86) PCT No.: PCT/IB2004/052060
§ 371 (c)(1),
(2), (4) Date: Jan. 3, 2007

(87) PCT Pub. No.: WO2005/038690
PCT Pub. Date: Apr. 28, 2005

(65) Prior Publication Data
US 2007/0176931 A1    Aug. 2, 2007

(30) Foreign Application Priority Data
Oct. 21, 2003  (EP) .................... 03103886

(51) Int. Cl.
*G06K 9/00*  (2006.01)
(52) U.S. Cl. .................................. 382/128
(58) Field of Classification Search .......... 382/100; 345/440; 600/300, 443, 510; 340/575, 870.07, 340/870.16; 704/201; 705/2
See application file for complete search history.

(56) References Cited

U.S. PATENT DOCUMENTS

| 4,483,346 | A | * | 11/1984 | Slavin | 600/523 |
| 4,513,743 | A |   | 4/1985 | van Arragon et al. | |
| 4,846,190 | A | * | 7/1989 | John | 600/544 |
| 4,931,864 | A | * | 6/1990 | Kawamura et al. | 358/519 |
| 4,974,598 | A | * | 12/1990 | John | 600/509 |
| 5,029,590 | A | * | 7/1991 | Allain et al. | 600/523 |
| 5,047,930 | A |   | 9/1991 | Martens et al. | |
| 5,487,755 | A | * | 1/1996 | Snell et al. | 607/27 |
| 5,792,198 | A | * | 8/1998 | Nappholz | 607/18 |
| 5,860,918 | A | * | 1/1999 | Schradi et al. | 600/300 |
| 5,946,407 | A | * | 8/1999 | Bamberger et al. | 382/132 |
| 6,173,068 | B1 | * | 1/2001 | Prokoski | 382/115 |
| 6,174,283 | B1 | * | 1/2001 | Nevo et al. | 600/301 |
| 6,409,659 | B1 | * | 6/2002 | Warner et al. | 600/300 |
| 6,471,658 | B1 | * | 10/2002 | Daniels et al. | 600/538 |
| 6,755,785 | B2 | * | 6/2004 | Omiya | 600/443 |
| 7,038,595 | B2 | * | 5/2006 | Seely | 340/870.07 |

(Continued)

FOREIGN PATENT DOCUMENTS

| EP | 0325851 | * | 8/1988 |
| WO | WO 93/18706 | * | 9/1993 |
| WO | WO 93/18706 A1 | | 9/1993 |

OTHER PUBLICATIONS

Chest; Prediction of Risk of Death Using 30-Day Outcome; Petra L. Graham and David A. Cook; Oct. 2004.*

(Continued)

*Primary Examiner* — Chan S Park
*Assistant Examiner* — Nancy Bitar (57) ABSTRACT

In a method of automatically displaying medical measurement data, a computer receives medical measurement data, automatically, in real time, converts the received measurement data into data for histograms, and outputs the converted data as picture signals. A readout (10) displays histogram columns (12) and a cumulative curve (14).

15 Claims, 8 Drawing Sheets

U.S. PATENT DOCUMENTS

| | | | |
|---|---|---|---|
| 7,720,306 B2 * | 5/2010 | Gardiner et al. | 382/276 |
| 2001/0031925 A1 * | 10/2001 | Mika et al. | 600/510 |
| 2001/0037067 A1 | 11/2001 | Tchou et al. | |
| 2003/0101076 A1 * | 5/2003 | Zaleski | 705/2 |
| 2003/0117296 A1 * | 6/2003 | Seely | 340/870.07 |
| 2003/0149597 A1 * | 8/2003 | Zaleski | 705/2 |

OTHER PUBLICATIONS

Sukuvaara, T., et al.; Object-Oriented Implementation of an Architecture for Patient Monitoring; 1993; IEEE Engineering in Medicine and Radiology; 2(4)69-81.

* cited by examiner

METHOD OF AUTOMATICALLY DISPLAYING MEDICAL MEASUREMENT DATA

The invention generally relates to medical monitoring systems and, in particular, to a method of automatically displaying medical measurement data.

Patient monitoring systems are used to monitor a patient's condition. Such systems display a multiplicity of medical measurement data. At present, it is possible, with a modern system, to measure and display up to 50 parameters, for example, in open-heart surgery. Most of the systems for displaying the measurement data simultaneously evaluate the measurement data and generate warning signals if one or more measured value(s) exceed(s) specified limit values.

Because of the multiplicity of indicated or displayed measured values, it is often difficult for medical personnel to quickly recognize critical conditions in a patient. This is essentially due to the fact that the personnel have to "filter out" the important information items from the displayed measurement data. This may result in a high cognitive loading of the personnel during critical events, for example, during an operation.

In order to be able to filter certain trends out of the measurement data displayed, it is known to use so-called graphic trend packets that can progressively display developing physiological changes. In particular, the correlation of physiological trend data helps the clinical personnel to assess a patient's condition correctly. Typically, this is achieved by overlapping trend graphs using a time cursor to collect individual trend data points.

However, this is very time-consuming since it requires a plurality of user inputs at a patient monitoring system. An indication of medical measured values would therefore be desirable that requires only a few user inputs, preferably none at all, and, at the same time, makes possible a good interpretability by clinical personnel.

This object is achieved by a method of automatically displaying clinical measured values.

The invention relates to a method of automatically displaying medical measurement data in which a computer receives the medical measurement data, automatically converts in real time the received measurement data into data for histograms and outputs the converted data as picture signals. The display of the medical measurement data in the form of histograms has the advantage over the conventional display of curve patterns of measurement signals and measured values in the form of numerical values that clinical personnel can recognize critical conditions in a patient and trends very quickly from the histograms and without additional user inputs. Real-time conversion of the medical measurement data histograms additionally ensures that the current condition of a patient is always displayed. In particular, a user of the method according to the invention can easily survey in real time the distribution of medical measurement data over time and does not have to actuate any user inputs at the monitoring system in order to obtain an overview of the pattern and distribution of the measurement data.

In particular, the measurement data are converted into dynamically updated real-time histogram readout objects. This further facilitates the indication and the evaluation of the medical measurement data by a user since the objects can be displayed, for example, in the form of windows on a desktop that is displayed by a graphic user interface on a viewing screen, such as is known, for example, from the known graphic user interfaces of computer operating systems.

During the conversion, the computer can generate aids for the retrospective analysis of histograms in the form of selectable functions that can be displayed on a viewing screen and output them together with the converted data combined as picture signals. The retrospective analysis makes possible a convenient and more precise evaluation of the measurement data displayed.

During the conversion, the computer may furthermore generate a cumulative curve indication of the medical measurement data and output it together with the converted data combined as picture signals in order to enable a long-term trend analysis.

Preferably, the computer processes control signals that are generated by input means communicating with the computer and that serve to control the conversion and/or the output of the picture signals. The input means may be a keyboard, a cursor or, alternately, a touch screen.

In accordance with a further aspect, the invention relates to a device for automatically displaying medical measurement data, comprising a computer that is designed for receiving medical measurement data, automatic real-time conversion of the received data into data for histograms and for outputting the converted data as picture signals.

In particular, the computer is designed to convert the measurement data into dynamically updated real-time histogram readout objects.

The computer may also be designed to generate, during the conversion, aids for the retrospective analysis of histograms in the form of selectable functions that can be displayed on a viewing screen and to output these together with the converted data combined as picture signals.

In a preferred embodiment, the computer is designed to generate, during the conversion, a cumulative curve readout of the medical measurement data and to output it together with the converted data combined as picture signals.

Finally, the computer may be designed to process control signals that are generated by an input means communicating with the computer and that serve to control the conversion and/or the output of the picture signals.

In accordance with a further aspect, the invention relates to a medical monitoring device that is characterized by a device as is explained above.

These and other aspects of the invention are apparent from and will be elucidated with reference to the embodiments described hereinafter.

In the description, in the claims, in the abstract and in the drawings, the terms used in the list of reference symbols cited at the back and associated reference symbols are used.

Figure 1:
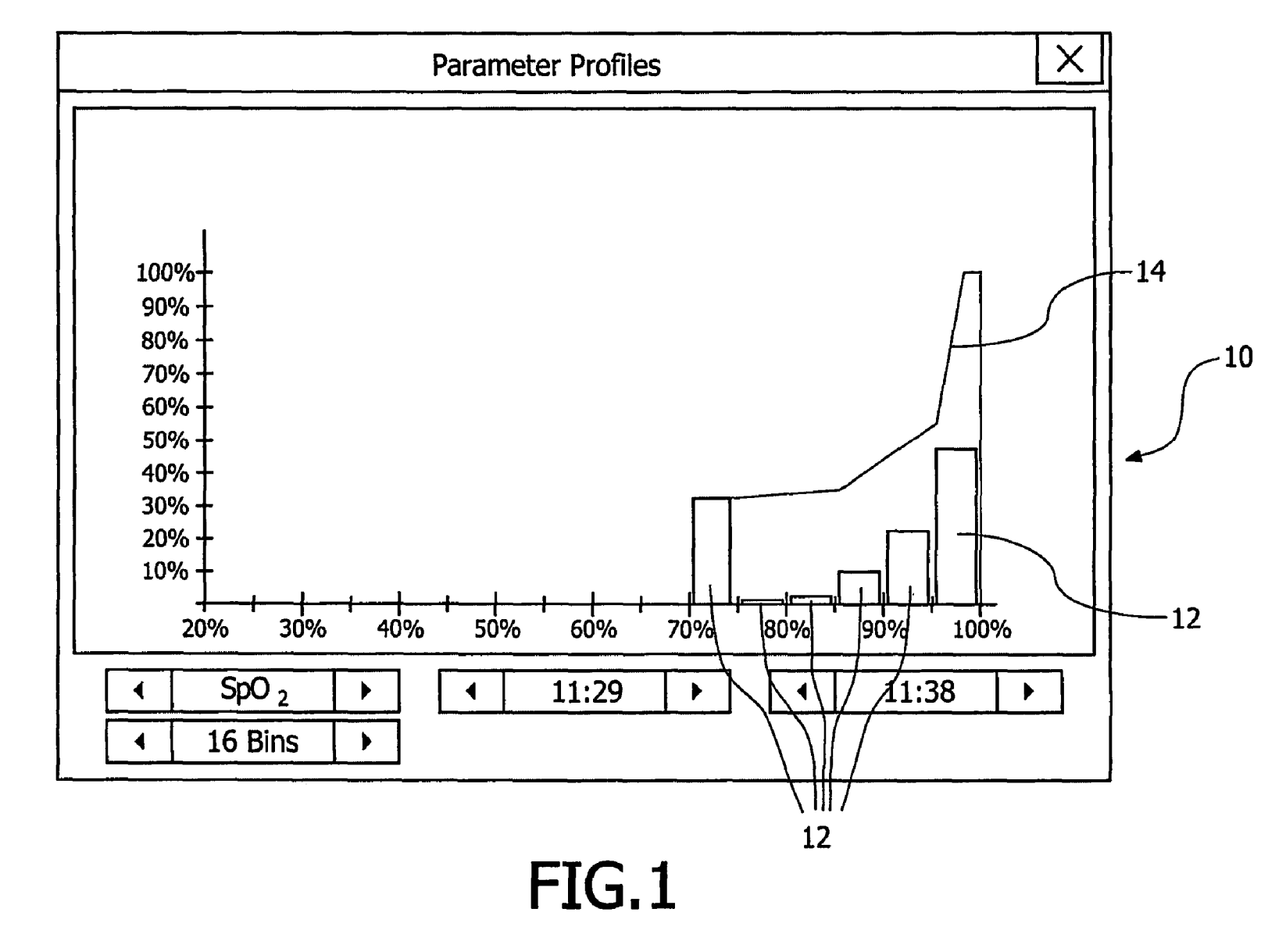
FIG. 1 shows a readout of a histogram and a cumulative curve in accordance with the invention.

FIG. 1 shows the underlying concept of a readout of a parameter histogram and a cumulative curve as can be displayed in accordance with the invention on the viewing screen of a patient monitoring device. For example, the SpO2 value (oxygen saturation of the blood) of a patient is monitored as medical measurement data. The SpO2 value is measured by means of a suitable sensor, not shown, whose measurement signals are transmitted in the form of medical measurement data to a computer, not shown, for example a suitably designed personal computer. The computer automatically generates picture signals from the received measurement data, which signals are transmitted to a viewing screen or monitor for display. If a personal computer is used as computer, it may be programmed in such a way that it processes the received measurement data, in particular converts them in real-time into histograms and outputs the converted data as picture signals so that they can be displayed as a histogram readout on the viewing screen or monitor mentioned.

The histogram readout 10 is formed by the time distribution of numerical measured values in histogram columns 12 that are definable by a user and are referred to below as "bins", and a cumulative curve 14 that is superimposed on the histogram columns. In the diagram contained in the readout shown in FIG. 1 and comprising a histogram and cumulative curve, the X-axis of the depicted diagram is the range of the medical measurement data or measured values used (for example, it is the range of numerical SpO2 values from 20% to 100% SpO2). The Y-axis of the diagram shows the relative value of the time of the measurements. The bin is the width of an individual histogram column (for example, for a setting with sixteen bins, the width of an individual bin is a 5% SpO2 value range).

The histogram readout is to be read as follows: the numerical SpO2 values were between 70% and 75% SpO2 during 30% of the measurement time. The time over which the data were accumulated in the histogram bins, for example a period of 8 hours, can be adjusted by the user. The cumulative curve is, at every point, the sum of all the previous bins. For example, a cursor that is shown at 60%/95% SpO2 means that the oxygen level falls below a value of 95% SpO2 for 60% of the measurement time.

In accordance with the invention, a plurality of parts may be provided that improve the display of medical measurement data:
1. A readout of a histogram and a cumulative curve, in which the objects displayed on a viewing screen are dynamically updated in real time; an instantaneous marker that displays the actual measured value in the histogram and, consequently, also in the context of the statistical distribution;
2. A histogram evaluation window and aids for the retrospective evaluation of a histogram (cumulative curve cursor, range-selection cursor and adjustable readout);
3. "Inop" bin: a separate bin ("inop bin") for displaying times of invalid or out-of-action measurement data as an indicator of the quality or representativeness of patient data or medical measurement data;
4. A deviation readout and a direction-change indicator, updated in real time on a quiescent readout of a patient;
5. Histogram snapshots and histogram trends: new aids for the visualization and comparison of parameter histograms over time periods; and
6. A combination of the parameter histogram view to form an event monitoring system and graphic trend applications.

Figure 2:
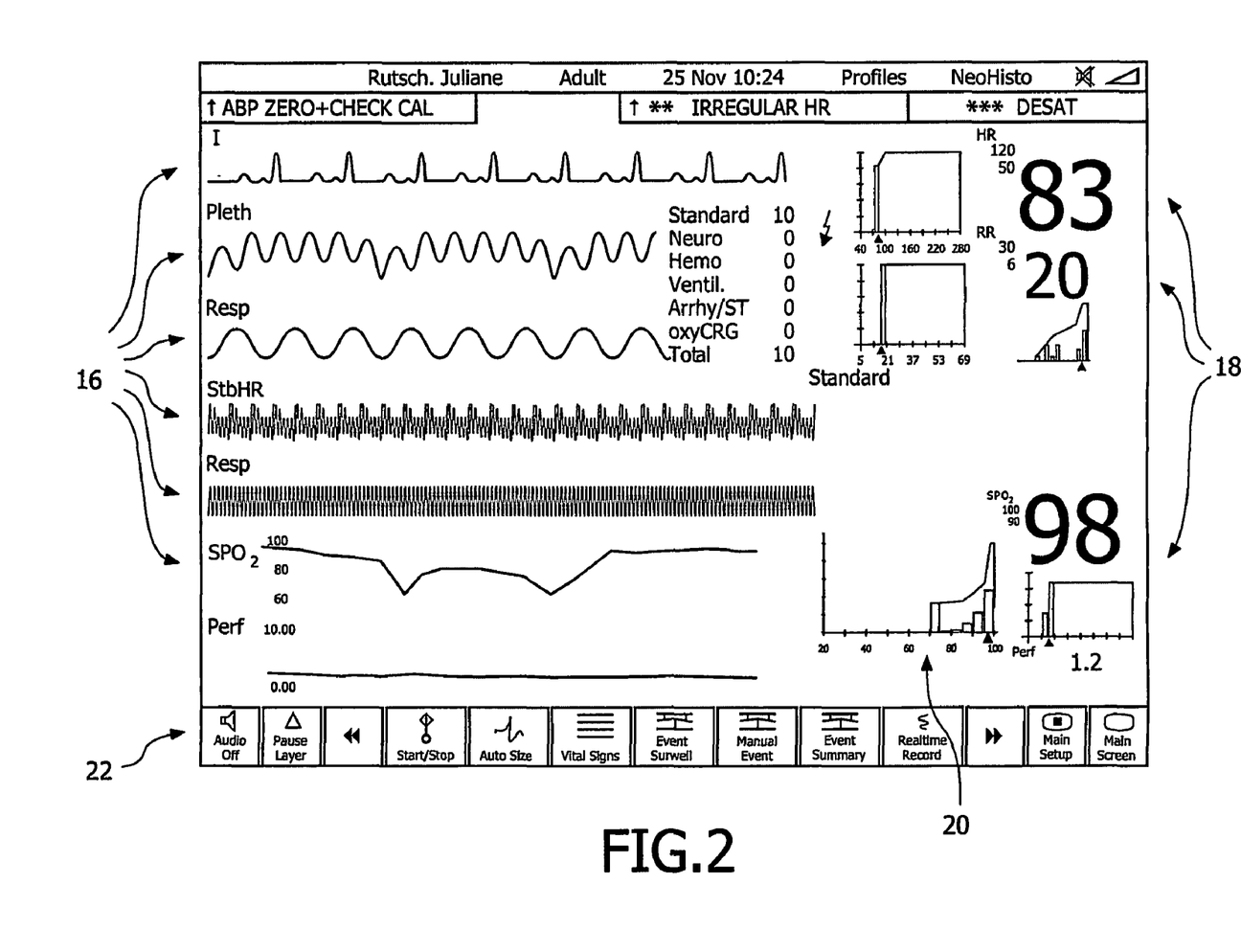
FIG. 2 shows a histogram readout as a viewing-screen object on a quiescent readout of a patient monitor.

Every individual part is described in detail below:

FIG. 2 shows the quiescent readout of a patient monitoring system that is typically formed from real-time wave shapes or real-time signal patterns 16 and numerical values 18 of the measured signals of the patient. The histogram readout and the cumulative curve 20 are a novel viewing-screen object that can be displayed on the quiescent readout alongside the associated measurement curves and numerical values.

The histogram readout on the viewing screen is dynamically updated in real time and makes it possible for a clinician to visualize changes in the parameter distribution. The marking under the X-axis shows in which bin the current numerical value is placed.

Figure 3:
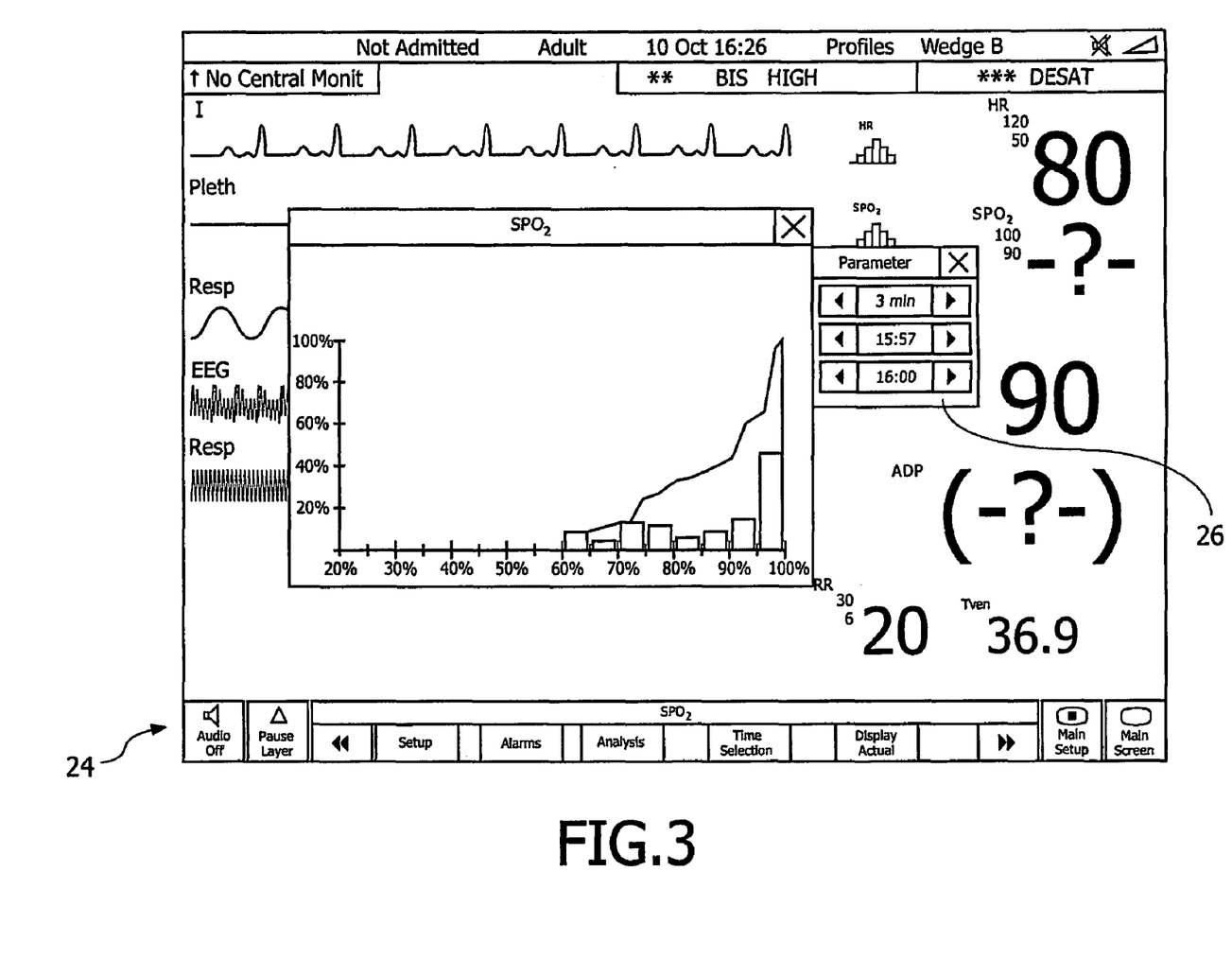
FIG. 3 shows a histogram analysis window.

Activation of any of the displayed histogram readout icons 22 makes the associated histogram analysis window clearly visible. Any of the numerical monitoring values may be displayed in the form of a histogram readout. As is shown in FIG. 3, the window comprises at its bottom a list of program function symbols 24 that make it possible for the user to call up further functions or aids for the histogram analysis. Selection of an offered function, for example of the analysis window, calls up a window comprising a list of functions 26 that are accessible.

In accordance with the invention, four analysis aids are available that support the user in obtaining further information items from the selected parameter histograms:
1. A cumulative curve cursor;
2. a range cursor;
3. a variability/stability readout (V/S); and
4. a deviation and direction-change readout.

Figure 4:
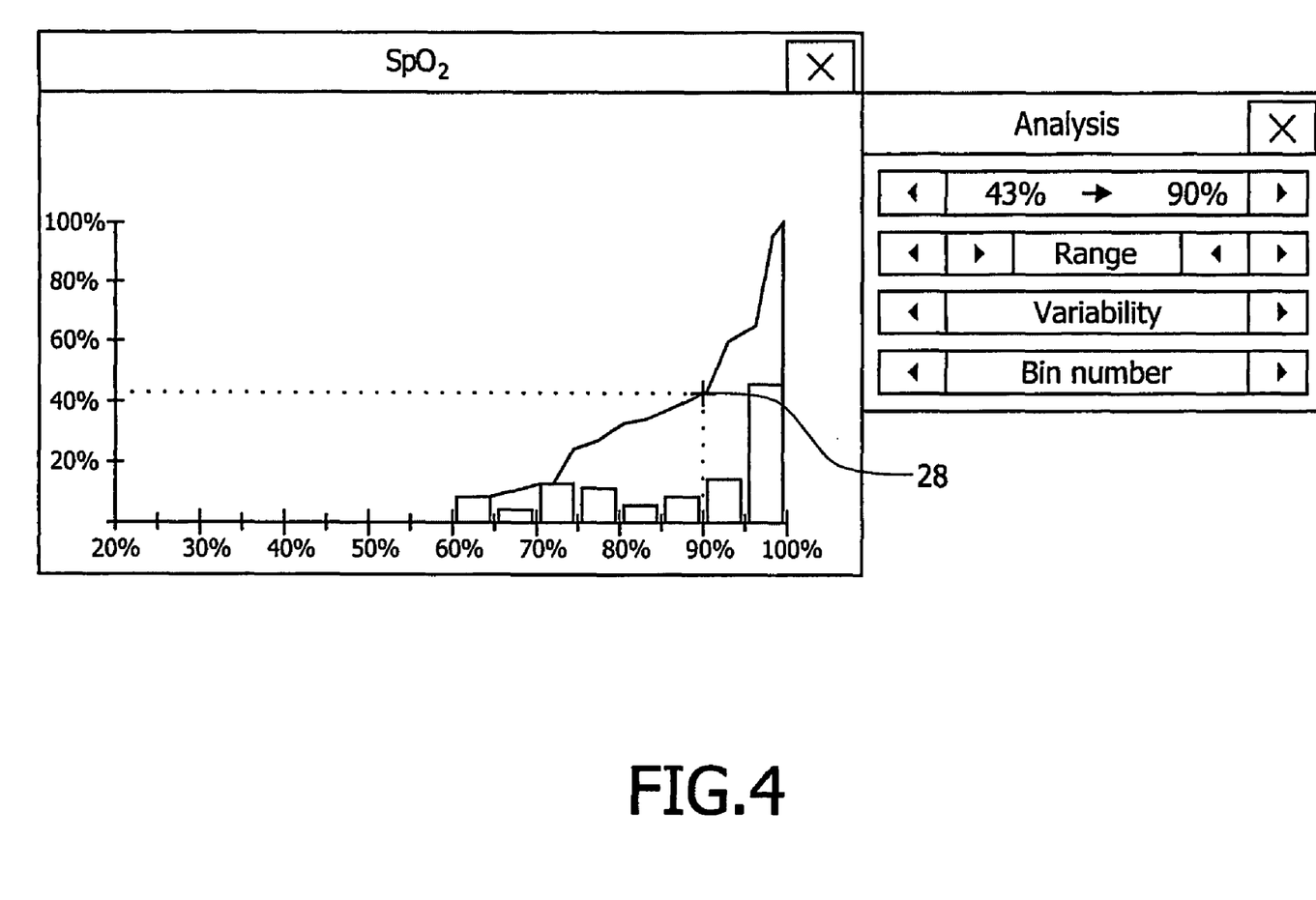
FIG. 4 shows a histogram analysis window with a cumulative cursor function.

In accordance with FIG. 4, a cursor aid 28 is available in order to investigate the cumulative curve to answer the following questions: for what percentage of the time were the SpO2 values below 90%? The answer is in the cursor field on the right (in the example shown in FIG. 4, the SpO2 saturation was less than 90% in 43% of the measurement time). The user can move the cursor along the cumulative curve by on-the-spot operation. Inputting the window always shows a standard value for the cumulative curve cursor (for example, the DESAT alarm limit of 80% for the SpO2 measurement).

Figure 5:
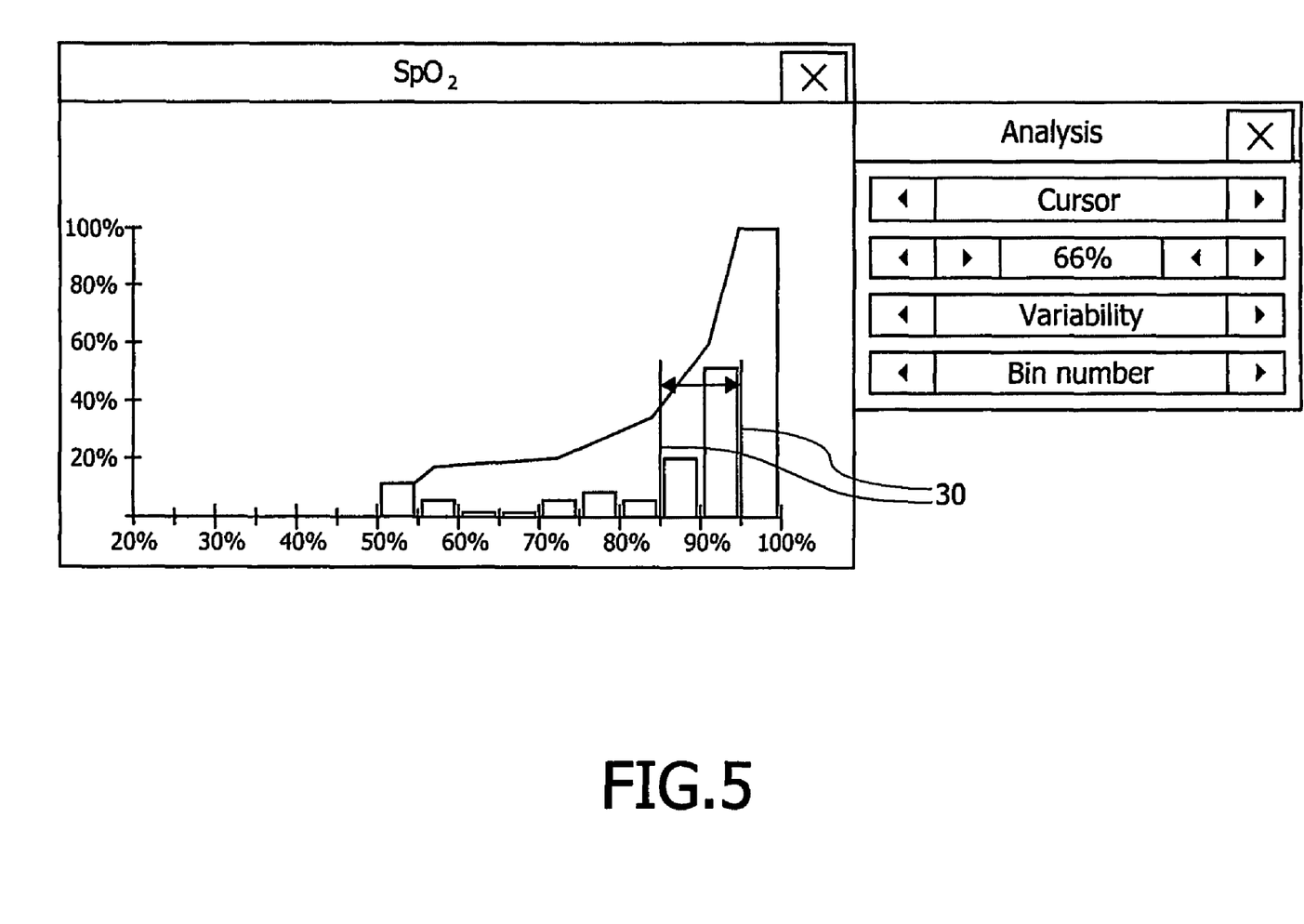
FIG. 5 shows a histogram analysis window with a range-selection cursor.

Range-selection cursors 30 make it possible for the user to determine the percentage of the time in which a numerical measured value was within the limits specified by the user. The cursors, which are shown in FIG. 5 by two vertical lines at about 85% and 95%, have, if a window is called up, the current lower and upper alarm limits of the measurement, shown as a histogram readout, as standard values. FIG. 5 shows that the SpO2 measured value was within the 85% to 95% range in 66% of the time.

Figure 6:
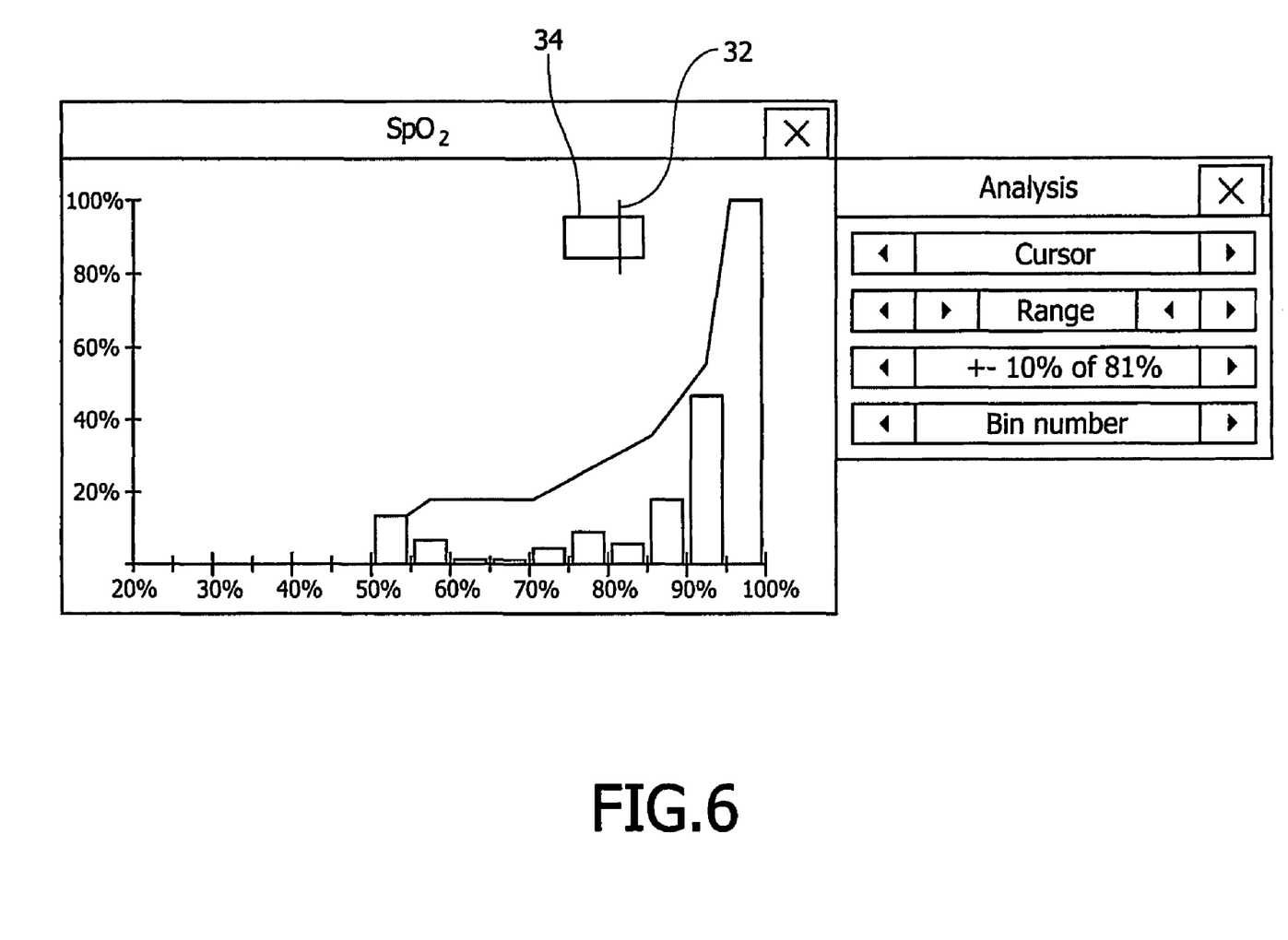
FIG. 6 shows a histogram analysis window with a variable readout.

The variability/stability readout provides information about the variability of the selected measurement and, consequently, about the stability of the patient's condition. Starting at a mean value (shown in FIG. 6 by a vertical marker), the "V/S" readout shows the range of the histogram in which the percentage of all the measurements that can be set by the user are situated. FIG. 6 shows 81% SpO2 as current mean value. A rectangle 34 is the range around the mean value that corresponds to the set variability of 10% in this example. The variability can be set by the user by means of the resolution of the predefined bin width (in the example shown, in steps of 10%).

Figure 7:
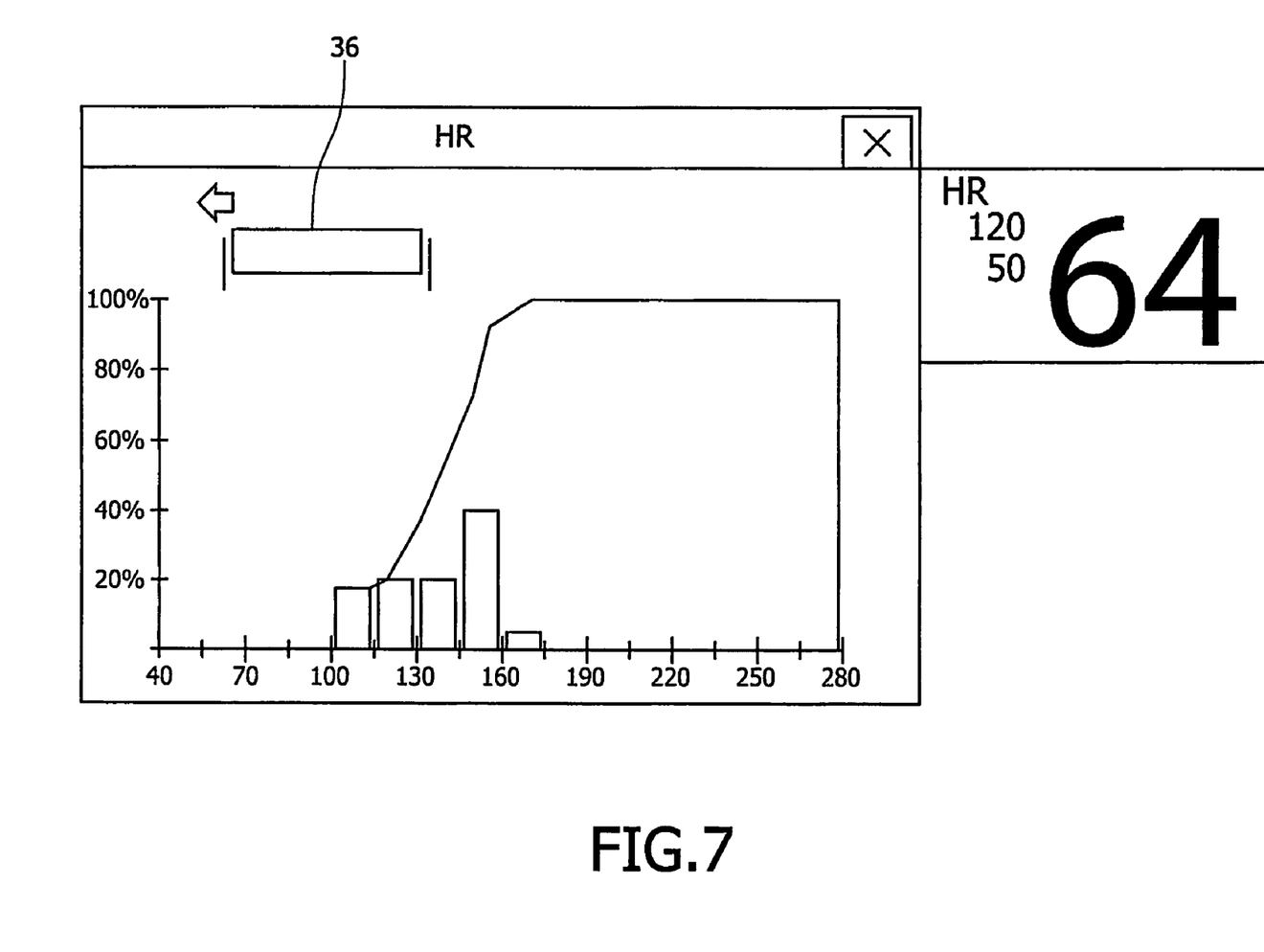
FIG. 7 shows a histogram analysis window with a deviation and trend readout.

FIG. 7 shows the current mean value as a continuous vertical line above the parameter histogram readout. In the present case the vertical line is located above the vertical bar above the value "130" on the horizontal axis, and just below the letter "H" in the HR graph title. The current deviation from this mean is shown graphically as a horizontal bar located to the left of the previously mentioned mean vertical line. The arrow shown above the deviation horizontal bar indicates the direction of the change in value comprising the deviation. A deviation above the mean value would be shown as a rectangular shaped range 36 to the right of the mean value, which is not shown in the current illustration. A deviation below the mean value would be shown on the left-hand side of the mean value, as is presented in the current illustration presently in FIG. 7.

Histogram analysis implies that numerical measured values are only taken into account if they are valid numerical values. However, in the case of noise or other interference that may be caused, inter alia, also by patients themselves or external effects of therapy measures, some measurement signals do not always result in valid numerical values. These periods of invalid (or out-of-action) data are relevant for the entire histogram statistics. The percentage of the time for which a measurement algorithm does not result in a valid numerical value is something that clinicians would like to know in order to be able to validate how relevant and statistically representative the collected data for an analysis are. In order to make this possible, in accordance with the invention, a special bin, denoted as "inop" is provided on the left of the lowest value range that is only displayed while the monitoring system is in a so-called configuration mode. The height of the "inop" bin enables clinicians to assess the relevance of the data displayed.

Figure 8:
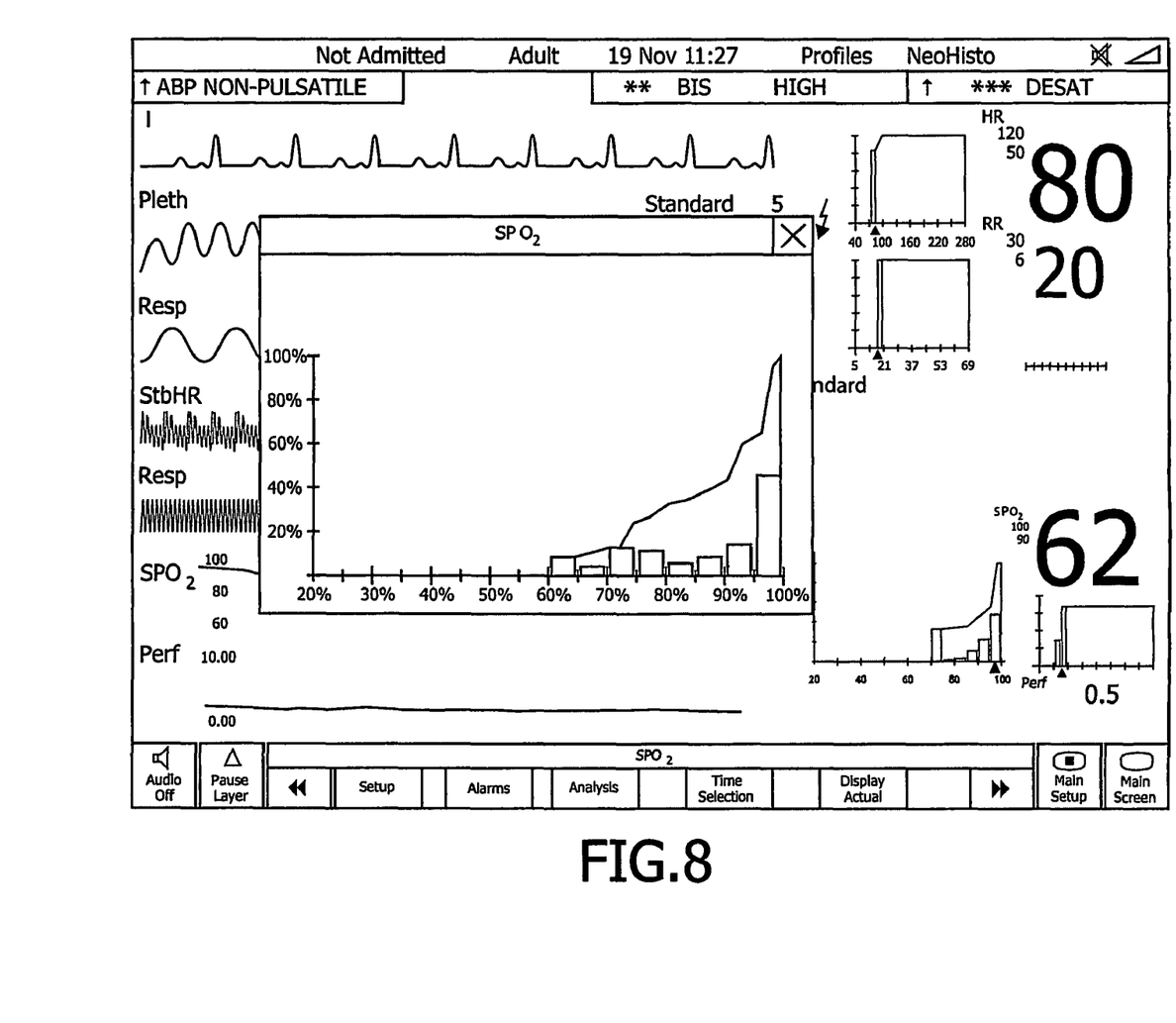
FIG. 8 shows a readout comprising histogram trends and histogram snapshots.

A further function comprises histogram snapshots and histogram trends that are stored for later reference and a later comparison, and for the purpose of documentation. Histogram trend is understood as meaning a readout that provides the clinician with the possibility of observing the changes in statistical distributions over time by stacking individual histograms or cumulative curves. In this way, for example, the current histogram can be compared with a previously recorded reference histogram and documented. In this connection, reference should be made to the viewing screen depicted in FIG. 8.

Finally, the invention also relates to a combination of the parameter histogram view to form an event monitoring system and a graphic view. In this connection, reference is made yet again to FIG. 1. The value distribution shows that, for example, a new-born patient has shown substantial periods in which a desaturation went down to 70% (currently, about 30% of the desaturation is in the region of 70%). In order to decide on a suitable treatment, the clinician needs detailed information items about the individual desaturation events. For example, whether apnea events and bradycardia events occurred during said desaturation periods. The sequence of apnea events and bradycardia events also provides indications about the type of apnea events (obstructive versus central or mixed). This can be achieved by combining the parameter histogram readout with the event monitoring packet, which makes it possible for the clinician to access a detailed episode view for individual events. A similar combination is also possible to form the graphic trend packet in order to display the content of the histogram as a graphic trend against time.

The clinical advantages of the invention are summarized yet again below and subdivided according to various users.

For the clinician, it is simpler and more intuitive to recognize the stability or the variability of individual measurement parameters of a patient using the invention, in particular even changes in condition. This improves a clinician's decision process.

A further advantage of the invention is that it supports a clinician, particularly in quickly answering the following exemplary questions:

For how long was a measurement parameter outside a predetermined range? The clinician can quickly answer this question by using the range-selection cursor explained above.

What was the distribution of the measured values over time? This indicates the stability of the measurements and supports the clinician in determining the therapy measures for a patient. The clinician can also quickly answer these questions by using the histogram readout explained above as a viewing-screen object on the quiescent readout and by using the deviation and change readout to display changes in real time.

Are therapeutic measurements effective enough to stabilize the patient? Improvements in the patient result can be monitored and the success of therapy methods can be assessed and can be documented in hitherto unavailable completeness by using the histogram snapshots and histogram trends.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

LIST OF REFERENCE SYMBOLS

10 Histogram readout
12 Histogram columns
14 Cumulative curve
16 Wave shapes or wave signal patterns
18 Numerical values
20 Histogram readout and cumulative curve
22 Histogram readout icons
24 List of program-function symbols
26 Window comprising a list of functions
28 Cursor aid
30 Range-selection cursor
32 Continuous vertical line
34 Rectangle
36 Rectangularly shaped range

The invention claimed is:

1. A method of automatically displaying medical measurement data in which a computer:
receives the medical measurement data,
automatically converts in real time the received measurement data into data for a histogram including updating the histogram in real time,
during the conversion, generates a cumulative curve indicative of the medical measurement data, the cumulative curve being cumulative of the series of histogram values, and
displays the histogram with the cumulative curve superimposed, the histogram and the cumulative curve having common axes and common scales.

2. The method as claimed in claim 1, further including:
filling the histogram with measurement data from a time window advancing in real time with selectable fixed length.

3. The method as claimed in claim 1, wherein, during the conversion, the computer generates aids for the retrospective analysis of the histogram in the form of selectable functions that can be displayed on a viewing screen and outputs them together with the converted data combined as picture signals.

4. The method as claimed in claim 3, wherein the retrospective analysis aids include at least one of:
a cumulative curve cursor for determining a percentage of time that histogram values are below a current cumulative cursor position;
range-selection cursors for determining a percentage of time that histogram values are within limits defined by the range-selection cursors;

a variability/stability readout that provides information about variability of the measurement data; and a deviation and direction-change readout that shows deviation from a mean histogram value and a direction of measurement data change.

5. The method as set forth in claim 1, further including:

displaying the histogram values as histogram columns and the cumulative curve is displayed as a curve superimposed on the histogram columns.

6. A medical monitoring device, comprising:

a display device for automatically displaying medical measurement data; and a computer programmed to perform the steps of:
receiving medical measurement data from a sensor device;
in real time, converting the medical measurement data into a histogram including a series of medical measurement values;
combining the series of medical measurement values of the histogram into a cumulative curve;
controlling the display device to display the cumulative curve superimposed on the histogram, the cumulative curve and the histogram sharing a common scale.

7. The medical monitoring device as claimed in claim 6, wherein the histogram and the cumulative curve are displayed with common axes.

8. A medical monitoring device comprising:

computer programmed for:
receiving medical measurement data,
automatically converting the medical measurement data into histogram data as the computer receives the medical measurement data,
generating a cumulative curve as the medical measurement data is received; and
a display device controlled to display the cumulative curve superimposed on the histogram data as the medical measurement data is received, the cumulative curve and the histogram data sharing common axes.

9. The medical monitoring device as claimed in claim 8, wherein the histogram and the cumulative curve are displayed superimposed with common scales.

10. The medical monitoring device as claimed in claim 9, further comprising the computer further being programmed for generating retrospective analysis aids including at least one of:

an inop bin displaying times of invalid or out of action measurement data;
a deviation readout;
a direction-change indicator;
a histogram snapshot and trends aid; and
a combination of a plurality of histograms.

11. The medical monitoring device as claimed in claim 9, further comprising an alarm indicator that is triggered when a measurement of histogram data is measured above or below a lower or upper alarm limit level.

12. The medical monitoring device as claimed in claim 9, wherein the histogram data is binned into histogram bins, the histogram bin size being definable by the user.

13. The medical monitoring device as claimed in claim 9, wherein the display further displays real-time signal patterns of the medical measurement data concurrently with the superimposed histogram values and cumulative curve.

14. The medical monitoring device as claimed in claim 9, wherein the histogram data includes a series of medical measurement values and the cumulative curve includes a sum of the medical measurement values.

15. A non-transitory computer readable medium storing a computer program for controlling a computer to perform the method of:

receiving medical measurement data;
converting in real time the received measurement data into data for a histogram including a continuously updated series of histogram values;
during the conversion, generating a cumulative curve indicative of the medical measurement data, the cumulative curve being cumulative of the series of histogram values; and,
outputting the cumulative curve superimposed on the histogram with common axes and scales, as picture signals.

* * * * *